US012690829B2

(12) United States Patent
Wang et al.

(10) Patent No.: US 12,690,829 B2
(45) Date of Patent: Jul. 28, 2026

(54) MEDICAL DEVICE AND C-ARM BASED DEVICE THEREOF

(71) Applicant: SHANGHAI UNITED IMAGING HEALTHCARE CO., LTD., Shanghai (CN)

(72) Inventors: Baojian Wang, Shanghai (CN); Guangbiao Chen, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 243 days.

(21) Appl. No.: 18/534,703

(22) Filed: Dec. 10, 2023

(65) Prior Publication Data

US 2024/0099681 A1     Mar. 28, 2024

Related U.S. Application Data

(63) Continuation of application No. PCT/CN2022/142892, filed on Dec. 28, 2022.

(30) Foreign Application Priority Data

Dec. 31, 2021 (CN) .......................... 202111665990.7
Dec. 31, 2021 (CN) .......................... 202123447288.1

(51) Int. Cl.
*A61B 6/00*        (2006.01)
*A61B 6/10*        (2006.01)
(52) U.S. Cl.
CPC ............ *A61B 6/4441* (2013.01); *A61B 6/105* (2013.01); *A61B 6/4476* (2013.01)

(58) Field of Classification Search
CPC .. A61B 6/00; A61B 6/10; A61B 6/105; A61B 6/4441; A61B 6/4452; A61B 6/4476; A61B 6/4405; A61B 6/4458
See application file for complete search history.

(56) References Cited

U.S. PATENT DOCUMENTS 5,627,873 A     5/1997 Hanover et al.
2008/0279340 A1 * 11/2008 Grebner ................. A61B 6/588
378/197
(Continued)

FOREIGN PATENT DOCUMENTS

CN     103784155 A     5/2014
CN     208525042 U     2/2019
(Continued)

OTHER PUBLICATIONS

The Extended European Search Report in European Application No. 22914933.1 mailed on Sep. 25, 2024, 6 pages.
(Continued)

*Primary Examiner* — Jurie Yun
(74) *Attorney, Agent, or Firm* — METIS IP LLC

(57) ABSTRACT

The present disclosure relates to a C-arm-based device. The C-arm-based device may include a C-arm component and a connection component. The C-arm component may include a first arm section and a second arm section. The connection component may include a first guiding section and a second guiding section separately disposed on a base. The first arm section is movably connected to the first guiding section. The second arm section is movably connected to the second guiding section.

20 Claims, 8 Drawing Sheets

1000

(56) References Cited

U.S. PATENT DOCUMENTS

| | | | |
|---|---|---|---|
| 2009/0024025 A1* | 1/2009 | Maschke ................ | A61B 6/505 606/86 R |
| 2009/0180592 A1 | 7/2009 | Gross et al. | |
| 2009/0185662 A1 | 7/2009 | Gross et al. | |
| 2014/0003576 A1 | 1/2014 | Graumann et al. | |

FOREIGN PATENT DOCUMENTS

| | | | |
|---|---|---|---|
| CN | 109480878 A | 3/2019 | |
| CN | 109893166 A | 6/2019 | |
| CN | 109925605 A | 6/2019 | |
| CN | 110833426 A | 2/2020 | |
| CN | 211334789 U | 8/2020 | |
| CN | 113152164 A | 7/2021 | |
| CN | 217390866 U | 9/2022 | |
| EP | 2095768 A1 | 9/2009 | |

OTHER PUBLICATIONS

International Search Report in PCT/CN2022/142892 mailed on Mar. 10, 2023, 5 pages.
Written Opinion in PCT/CN2022/142892 mailed on Mar. 10, 2023, 5 pages.
First Office Action in Chinese Application No. 202111665990.7 mailed on Feb. 27, 2026, 19 pages.

* cited by examiner

1000

8100

MEDICAL DEVICE AND C-ARM BASED DEVICE THEREOF

CROSS-REFERENCE TO RELATED APPLICATIONS

This application is a continuation of International Application No. PCT/CN2022/142892, filed on Dec. 28, 2022, which claims priority of Chinese Patent Application No. 202111665990.7 filed on Dec. 31, 2021 and Chinese Patent Application No. 202123447288.1 filed on Dec. 31, 2021, the contents of each of which are incorporated herein by reference.

TECHNICAL FIELD

The present disclosure generally relates to medical-related devices, and in particular, to a C-arm-based device.

BACKGROUND

Generally, a C-arm-based device is a bracket with a C shape, which includes two arm sections configured to support devices. For example, the two arm sections may be configured to support a radiation generator and a radiation detector respectively. In some cases, when a medical device including the C-arm-based device is used, a distance between the radiation generator and the radiation detector may need to be adjusted according to actual needs. Therefore, it is desirable to provide an improved C-arm-based device or a medical device including a C-arm-based device easy to disassemble and maintain.

SUMMARY

An aspect of the present disclosure relates to a C-arm-based device. The C-arm-based device may include a C-arm component and a connection component. The C-arm component may include a first arm section and a second arm section. The connection component may include a first guiding section and a second guiding section separately disposed on a base. The first arm section is movably connected to the first guiding section. The second arm section is movably connected to the second guiding section.

In some embodiments, the first guiding section and the second guiding section may be collinear to each other.

In some embodiments, the first guiding section or the second guiding section may include two guiding units parallel to each other.

In some embodiments, the first arm section may be movably connected to the first guiding section via at least one first slider disposed on the first guiding section. The second arm section may be movably connected to the second guiding section via at least one second slider disposed on the second guiding section.

In some embodiments, the C-arm-based device may further include an anti-collision block detachably disposed on the first guiding section and/or the second guiding section.

In some embodiments, the anti-collision block may include a first part detachably disposed on the first guiding section and a second part detachably disposed on the second guiding section.

In some embodiments, the anti-collision block may include a plurality of bulges configured to position the first guiding section and/or the second guiding section.

In some embodiments, the C-arm-based device may further include a stretchable protective component connected with the first arm section and the second arm section respectively.

In some embodiments, the C-arm-based device may further include a driving component configured to drive the first arm section and/or the second arm section to move toward or away from each other along a length direction of the connection component.

In some embodiments, the driving component may include a drive acquisition mechanism and a driver configured to drive the drive acquisition mechanism to rotate to drive the first arm section and/or the second arm section to move toward or away from each other.

In some embodiments, the driving component may further include a first fixed part and a second fixed part. The first fixed part may include two detachable portions that are connected to the drive acquisition mechanism and the first arm section respectively. The second fixed part may include two detachable portions that are connected to the drive acquisition mechanism and the second arm section respectively.

In some embodiments, the driving component may further include a first drive conversion mechanism connected to the first arm section, a second drive conversion mechanism connected to the second arm section, and a drive transmission mechanism connected with the first drive conversion mechanism and the second drive conversion mechanism. The drive transmission mechanism may be configured to transmit drive of the drive acquisition mechanism to the first drive conversion mechanism and/or the second drive conversion mechanism to guide the first drive conversion mechanism and/or the second drive conversion mechanism to move to drive the first arm section and/or the second arm section to move toward or away from each other.

In some embodiments, the first drive conversion mechanism or the second drive conversion mechanism may include a main conversion assembly and a secondary conversion assembly. The main conversion assembly may be connected with the drive transmission mechanism. The drive transmission mechanism may drive the main conversion assembly to rotate. The secondary conversion assembly may be connected with the main conversion assembly and the first arm section or the second arm section. The main conversion assembly may convert rotation of the main conversion assembly into a linear motion of the secondary conversion assembly to drive the first arm section or the second arm section.

In some embodiments, in response to that the drive transmission mechanism simultaneously guides the first drive conversion mechanism and the second drive conversion mechanism to move, the secondary conversion assemblies of the first drive conversion mechanism and the second drive conversion mechanism may move in opposite directions.

In some embodiments, in response to that the drive transmission mechanism simultaneously guides the first drive conversion mechanism and the second drive conversion mechanism to move, the secondary conversion assemblies of the first drive conversion mechanism and the second drive conversion mechanism may move in a same direction. Moving speeds of the secondary conversion assemblies may be different or the same.

In some embodiments, the first drive conversion mechanism or the second drive conversion mechanism may include a screw-nut mechanism. The main conversion assembly may be a screw and the secondary conversion assembly may be a nut.

In some embodiments, the first drive conversion mechanism or the second drive conversion mechanism may include a gear-rack mechanism. The main conversion assembly may be a gear and the secondary conversion assembly may be a rack.

In some embodiments, the drive transmission mechanism may include a first rotating wheel, at least one first bevel gear disposed in the first rotating wheel, and two second bevel gears meshing with the at least one first bevel gear. A central axis of the at least one first bevel gear may be perpendicular to a central axis of the first rotating wheel. The first rotating wheel may rotate to drive the at least one first bevel gear to rotate around the central axis of the first rotating wheel. The two second bevel gears may be coaxial with the first rotating wheel and respectively coaxially fixed with main conversion assemblies of the first drive conversion mechanism and the second drive conversion mechanism to respectively guide the first drive conversion mechanism and the second drive conversion mechanism to move.

In some embodiments, the drive acquisition mechanism may include a driving shaft, a second rotating wheel fixed coaxially with the first rotating wheel, and a third rotating wheel meshing with the second rotating wheel and fixed coaxially with the driving shaft.

In some embodiments, the driving component may further include two brakes respectively configured to stop or release the rotation of the main conversion assemblies of the first drive conversion mechanism and the second drive conversion mechanism.

A further aspect of the present disclosure relates to a medical device. The medical device may include a base, a C-arm-based device, and a robot body. The C-arm-based device may include a C-arm component and a connection component. The C-arm component may include a first arm section and a second arm section. The connection component may include a first guiding section and a second guiding section separately disposed on a base. The first arm section is movably connected to the first guiding section. The second arm section is movably connected to the second guiding section. The robot body may be rotatably connected to the base and configured to drive the C-arm-based device to move in space.

A further aspect of the present disclosure relates to a C-arm-based device. The C-arm-based device may include a first arm section, a second arm section, and a driving component. The driving component may include a drive acquisition mechanism, a first drive conversion mechanism, a second drive conversion mechanism, a drive transmission mechanism. The drive acquisition mechanism may be configured to acquire drive. The first drive conversion mechanism may be connected to the first arm section. The second drive conversion mechanism may be connected to the second arm section. The drive transmission mechanism may be connected with the first drive conversion mechanism and the second drive conversion mechanism. The drive transmission mechanism may be configured to transmit the drive of the drive acquisition mechanism to the first drive conversion mechanism and/or the second drive conversion mechanism to guide the first drive conversion mechanism and/or the second drive conversion mechanism to move to drive the first arm section and/or the second arm section to move toward or away from each other.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

Figure 1:
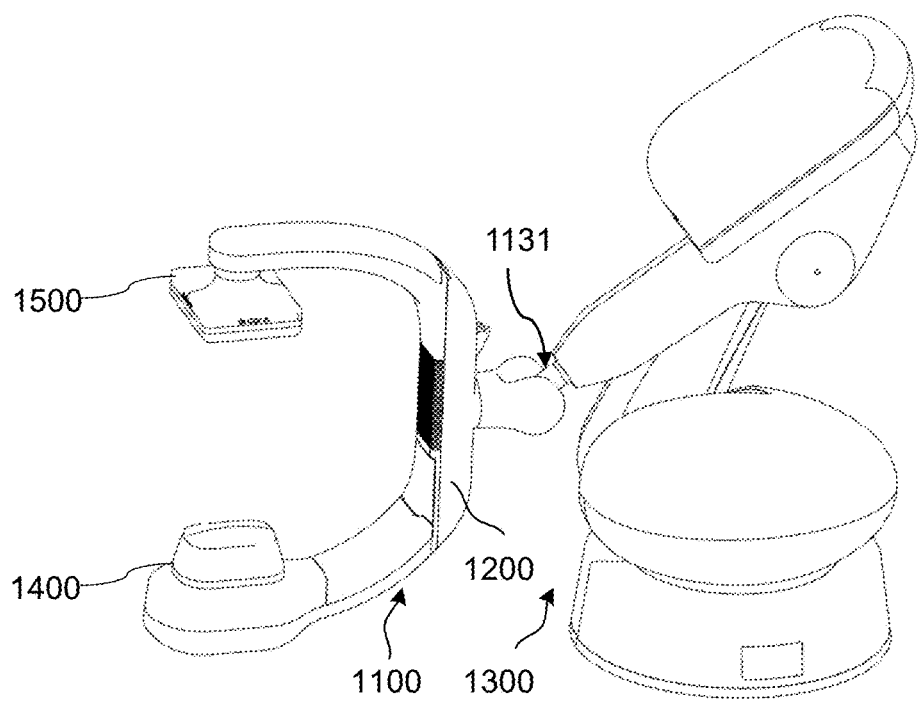
FIG. 1 is a schematic diagram illustrating an exemplary medical device according to some embodiments of the present disclosure.

Reference numerals and represented structures:

1000—medical device, 1100—C-arm-based device, 1200—base, 1300—robot body, 1400—radiation generator, 1500—radiation detector, 1131—rotating shaft, 2100—C-arm-based device, 2110—C-arm component, 2111—first arm section, 2112—second arm section, 2120—connection component, 2121—first guiding section, 2122—second guiding section, 2123—seam, 2131—first slider, 2132—second slider, 2140—anti-collision block, 2141—bulges, 2150—stretchable protective component, 2151—cover, 2152—fixed units, 2153—fixed rope, 2160—driving component, 2161—driving shaft, 2162—first fixed part, X—guiding unit, Y—guiding unit, U—guiding unit, V—guiding unit, M—detachable portion, N—detachable portion, 2200—base, 8100—C-arm-based device, 8111—first arm section, 8160—driving component, 8112—second arm section, 8161—first drive conversion mechanism, 81611—main conversion assembly 81611, 81612—secondary conversion assembly, 8162—second drive conversion mechanism, 81621—main conversion assembly 81611, 81622—secondary conversion assembly, 8163—drive transmission mechanism, 81631—first rotating wheel, 81632—first bevel gear, 81633—second bevel gear, 8164—drive acquisition mechanism, 81641—driving shaft, 81642—second rotating wheel, 81643—third rotating wheel, 8165—driver, 8166—brake, 8167—brake, 8200—base.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by another expression if they achieve the same purpose.

It will be understood that when a unit, engine, module, or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Generally, there have been medical devices used in the fields of angiography, cardiology, and neurology. These medical devices usually include a C-arm-based device. A radiation generator (e.g., an X-ray generator) and a radiation detector are respectively arranged in the both ends of the C-arm-based device. The C-arm-based device is arranged on a medical robot and may be rotated at any angle in space under the action of the medical robot. The C-arm-based device may be provided with two arm sections, which may be assembled with each other to form the C-arm-based device. In a process of clinical diagnosis, in order to obtain a relatively large degree of clinical freedom, the two arm sections of the C-arm-based device may move toward or away from each other. Specifically, one arm section is fixed relative to the medical robot, and the other arm section is movable relative to the medical robot, so that a relative movement of the two arm sections is realized, thereby changing a relative distance between the two arm sections, accordingly, a relative distance between the radiation generator and the radiation detector may be changed. With the continuous development of medical technology, in order to obtain larger degree of clinical freedom (i.e., a larger relative distance between the radiation generator and the radiation detector), the two arm sections of the C-arm-based device need to be both are movably arranged on the medical robot, which can be understood as a C-arm-based device with two movable arm sections. However, the C-arm-based device with two movable arm sections is complicated and cumbersome to disassemble, assemble and maintain, resulting in poor serviceability.

An aspect of the present disclosure provides a C-arm-based device. The C-arm-based device may include a C-arm component and a connection component. The C-arm component may include a first arm section and a second arm section. The connection component may include a first guiding section and a second guiding section separately disposed on a base. The first arm section may be movably connected to the first guiding section. The second arm section may be movably connected to the second guiding section. According to some embodiments of the present disclosure, the first arm section and/or the second arm section of the C-arm-based device may be driven to move, on the first guiding section and/or the second guiding section, toward or away from each other, thereby adjusting a distance between the first arm section and the second arm section. In addition, the first guiding section and the second guiding section are separately disposed on the base. When one of the first arm section and the second arm section needs to be disassembled for maintenance, it is only necessary to disassemble the arm section from its corresponding guiding section or disassemble the arm section and its corresponding guiding section from the base, thereby optimizing the independence of the two arm sections of the C-arm-based device, simplifying the maintenance process of the C-arm-based device, and improving the serviceability of the C-arm-based device. In some embodiments, the C-arm-based device may be applied to various occasions. For example, the C-arm-based device may be applied to fields of angiography, cardiology, neurology, etc. As another example, the C-arm-based device may be used in a medical device such as a digital subtraction angiography (DSA).

FIG. 1 is a schematic diagram illustrating an exemplary medical device according to some embodiments of the present disclosure. As shown in FIG. 1, the medical device 1000 may include a C-arm-based device 1100, a base 1200, and a robot body 1300.

The C-arm-based device 1100 may be configured to support a medical component, for example, a radiation generator 1400, a radiation detector 1500, etc. In some embodiments, the radiation generator 1400 may be a device that can emit rays (e.g., X-rays, gamma rays, electronic rays); the radiation detector 1500 may be a device that can receive the rays emitted by the radiation generator 1400. Through the cooperation of the radiation generator 1400 and the radiation detector 1500, a medical operation such as a medical examination or a medical treatment may be performed. Merely by way of example, the radiation generator 1400 may be an X-ray generator that can emit X-rays; the radiation detector 1500 may be a flat panel detector. Accordingly, the medical device 1000 may be an angiography device (e.g., a digital subtraction angiography (DSA) device) that can perform an angiography imaging operation.

Figure 2:
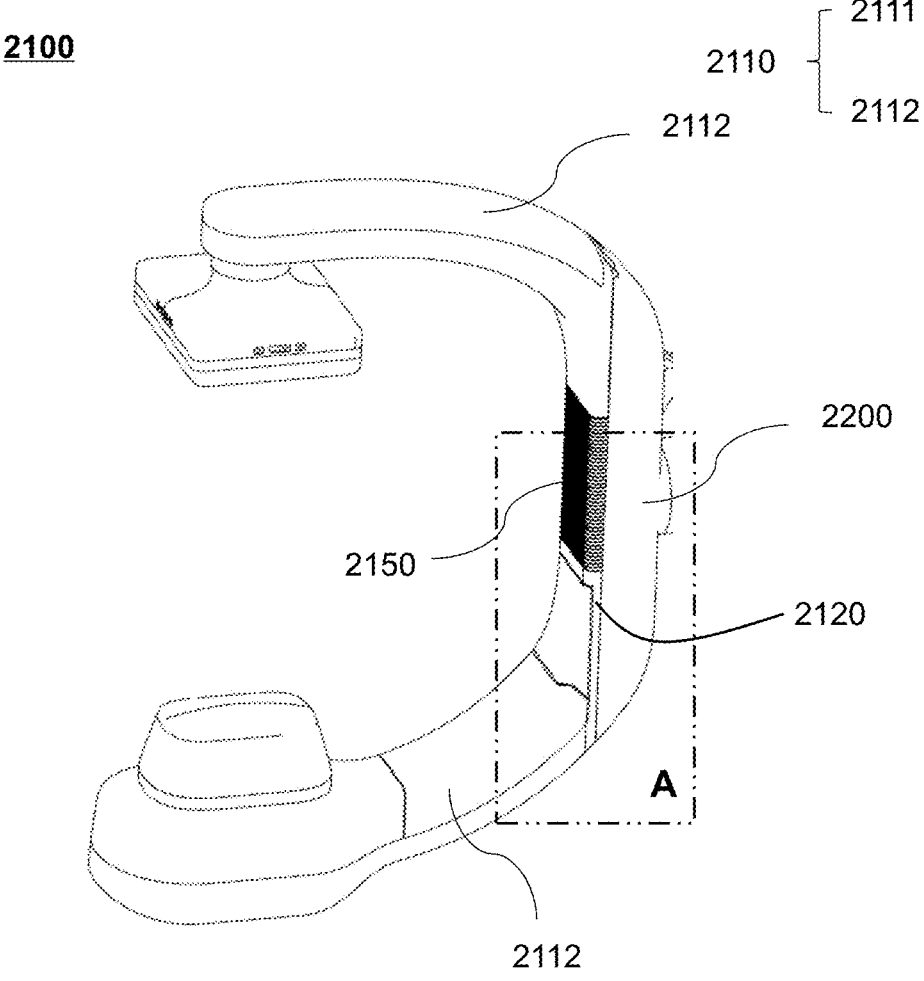
FIG. 2 is a schematic diagram illustrating an exemplary C-arm-based device according to some embodiments of the present disclosure.

In some embodiments, the C-arm-based device 1100 may include a C-arm component including a first portion (e.g., a first arm section 2111 illustrated in FIG. 2) and a second portion (e.g., a second arm section 2112 illustrated in FIG. 2). In some embodiments, the first portion and the second portion may be configured to support different medical components. For example, the first portion may be configured to support the radiation generator 1400 and the second portion may be configured to support the radiation detector 1500. In some embodiments, the first portion and the second portion may be separately connected with each other. Accordingly, a distance between the radiation generator 1400 and the radiation detector 1500 can be adjusted by adjusting a relative distance between the first portion and the second portion, which can meet various clinical requirements. More descriptions regarding the C-arm-based device 1100 may be found elsewhere in the present disclosure, for example, FIG. 2 and the descriptions thereof.

The robot body 1300 may be rotatably connected to the C-arm-based device 1100 via the base 1200 and configured to drive the C-arm-based device 1100 to move in space. For example, the robot body 1300 may drive the C-arm-based device 1100 to rotate and/or linearly move in space, so that the C-arm-based device 1100 has relatively high spatial flexibility, thereby meeting different clinical requirements. In some embodiments, the robot body 1300 may include a six-axis robot. In some embodiments, the robot body 1300 may include a rotating shaft 1131, an end of which may be rotatably connected to the base 1200. Accordingly, the robot body 1300 can drive the C-arm-based device 1100 to rotate around the rotating shaft 1131 to change a spatial position of the first portion of the C-arm based device 1100, a spatial position of the second portion of the C-arm based device 1100, and/or a position of a plane where the first portion and/or the second portion are located, thereby increasing a spatial range of the motion of the C-arm-based device 1100.

In some embodiments, a couch (not shown) configured to support a patient may be provided between the radiation generator 1400 and the radiation detector 1500. Before a clinical operation is performed, the C-arm-based device 1100 may be driven by the robot body 1300 to rotate to adjust a position of the radiation generator 1400, a position of the radiation detector 1500, a distance between the radiation generator 1400 and the radiation detector 1500, etc., thereby meeting various clinical requirements.

It should be noted that the above description of the medical device 1000 is merely provided for the purposes of illustration, and not intended to limit the scope of the present disclosure. For persons having ordinary skills in the art, multiple variations and modifications may be made under the teachings of the present disclosure. For example, the medical device 1000 may include one or more additional components and/or one or more components of the medical imaging system 1000 described above may be omitted.

Figure 3:
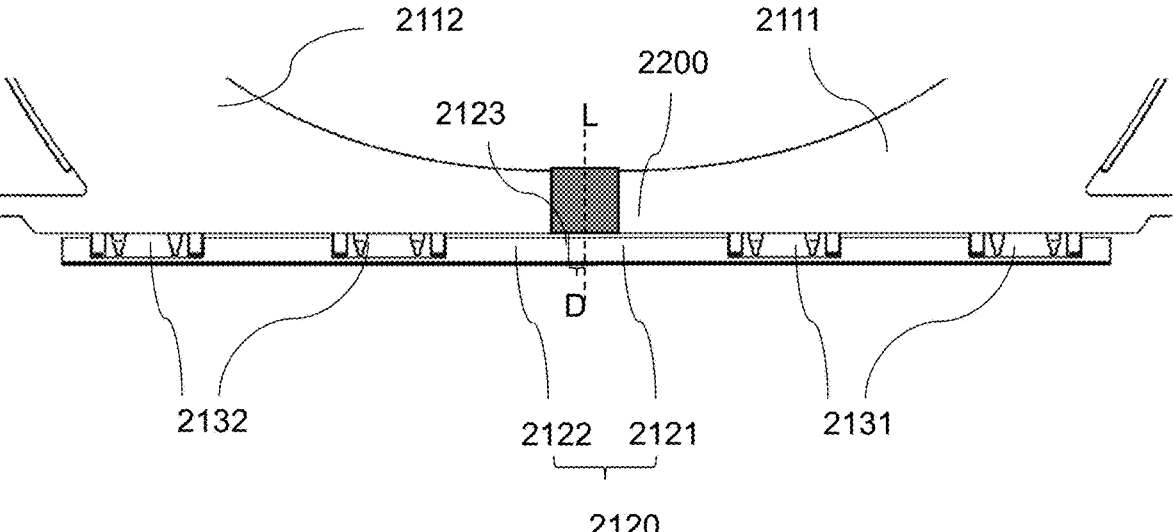
FIG. 3 is a schematic diagram illustrating an exemplary connection component of a C-arm-based device according to some embodiments of the present disclosure.

FIG. 2 is a schematic diagram illustrating an exemplary C-arm-based device according to some embodiments of the present disclosure. FIG. 3 is a schematic diagram illustrating an exemplary connection component of the C-arm-based device according to some embodiments of the present disclosure. In some embodiments, the C-arm-based device 2100 is an exemplary embodiment of the C-arm-based device 1100 illustrated in FIG. 1.

As shown in FIG. 2, the C-arm-based device 2100 may include a C-arm component 2110 and a connection component 2120.

The C-arm component 2110 may include a first arm section 2111 and a second arm section 2112. The first arm section 2111 and the second arm section 2112 may be assembled with each other to form the C-arm component 2110. More detailed descriptions of the first arm section 2111 or the second arm section 2112 may be found elsewhere in the present disclosure, for example, FIG. 7 and descriptions thereof.

The connection component 2120 may be disposed on a base 2200 (which may be an exemplary embodiment of the based 1200 illustrated in FIG. 1) and located between the first arm section 2111 and the second arm section 2112. In some embodiments, the connection component 2120 may be configured to movably connect the first arm section 2111 and the second arm section 2112.

In some embodiments, as shown in FIG. 3, the connection component 2120 may include a first guiding section 2121 and a second guiding section 2122. In some embodiments, the first arm section 2111 may be movably connected to the first guiding section 2121 and may slide through the first guiding section 2121; the second arm section 2112 may be movably connected to the second guiding section 2122 and may slide through the second guiding section 2122. In some embodiments, the first guiding section 2121 and the second guiding section 2122 may be manufactured separately or may be obtained by cutting an integrated slide rail.

In some embodiments, the first guiding section 2121 and the second guiding section 2122 may be separately and detachably disposed on the base 2200. Accordingly, the first guiding section 2121 and the second guiding section 2122 can be disassembled and/or assembled independently. For example, the first guiding section 2121 and the second guiding section 2122 may be installed on the base 2200 by screws, rivets, or connected to the base 2200 by snaps.

In some embodiments, the first guiding section 2121 and the second guiding section 2122 may be assembled on the base 2200, and then the first arm section 2111 and the second arm section 2112 may be respectively assembled on the first guiding section 2121 and the second guiding section 2122. Accordingly, the first arm section 2111 and the second arm section 2112 can be respectively disassembled from the first guiding section 2121 and the second guiding section 2122.

In some embodiments, the first arm section 2111 and the second arm section 2112 may be respectively assembled on the first guiding section 2121 and the second guiding section 2122, and then the first arm section 2111 and the first guiding section 2121 may be assembled on the base 2200 as a whole; the second arm section 2112 and the second guiding section 2122 may be assembled on the base 2200 as a whole. Accordingly, the first arm section 2111 and the first guiding section 2121 can be disassembled from the base 2200 as a whole; the second arm section 2112 and the second guiding section 2122 can be disassembled from the base 2200 as a whole.

Generally, the first arm section 2111 and the second arm section 2112 may be assembled on a same guiding section. In such cases, during assembling, the first arm section 2111 and the second arm section 2112 need to be assembled on the guiding section, and then the first arm section 2111, the second arm section 2112, and the guiding section are assembled on the base 2200 as a whole. When one of the first arm section 2111 and the second arm section 2112 needs to be disassembled for maintenance, the first arm section 2111, the second arm section 2112, and the guiding section need to be disassembled from the base 2200 as a whole, which is time-consuming and labor-intensive, and is prone to safety risks. According to the above embodiments of the present disclosure, through the first arm section 2111, the second arm section 2112, the first guiding section 2121, and the second guiding section 2122, the disassembly and assembly of the first arm section 2111 and the first guiding section 2121 or the disassembly and assembly of the second arm section 2112 and the second guiding section 2122 can be performed simultaneously (e.g., by multiple workers). When one of the first arm section 2111 and the second arm section 2112 needs to be disassembled for maintenance, it is only necessary to disassemble the arm section to be maintained from the corresponding guiding section or disassemble the arm section to be maintained and the corresponding guiding section from the base 2200, thereby simplifying the maintenance process of the C-arm-based device 2100 and improving the serviceability of the C-arm-based device 2100.

In some embodiments, as shown in FIG. 3, the first guiding section 2121 and the second guiding section 2122 may be collinear to each other. In some embodiments, the first guiding section 2121 and/or the second guiding section 2122 may have a belt-like or plate-like planar structure. In some embodiments, extension directions of the first guiding section 2121 and the second guiding section 2122 may be parallel. In some embodiments, the first guiding section 2121 and the second guiding section 2122 may abut against each other. In some embodiments, an abutting sectional area (or sectional shape) of the first guiding section 2121 and an abutting sectional area (or sectional shape) of the second guiding section 2122 may be the same or substantially the same, which can improve the conformity of the abutting of the first guiding section 2121 and the second guiding section 2122. Accordingly, when it is necessary to inspect or maintain a component (e.g., cable(s) located within the base 2200, the first guiding section 2121, the second guiding section 2122) covered by the first arm section 2111 or a portion thereof and/or the second arm section 2112 or a portion thereof, the arm section or a portion thereof that covers the component can be pushed along the first guiding section 2121 and the second guiding section 2122, thereby simplifying the maintenance process of the C-arm-based device 2100 and improving the serviceability of the C-arm-based device 2100.

In some embodiments, a positioning shoulder (not shown) may be provided on one side of the base 2200. The positioning shoulder may be configured to restrict an assembly position of the first guiding section 2121 and the second guiding section 2122 to cause the first guiding section 2121 and the second guiding section 2122 to be collinear to each other.

In some embodiments, as shown in FIG. 3, there may be a seam 2123 between the first guiding section 2121 and the second guiding section 2122. In some embodiments, a distance (e.g., D illustrated in FIG. 3) between the seam 2123 and a center line L of the base 2200 may be larger than a distance threshold to reduce the impact of the seam 2123 on the strength of the C-arm-based device 2100. In some embodiments, the distance threshold may be an empirical value (e.g., 1 cm, 3 cm, 5 cm, 10 cm) or may be adjustable under different situation.

Figure 7:
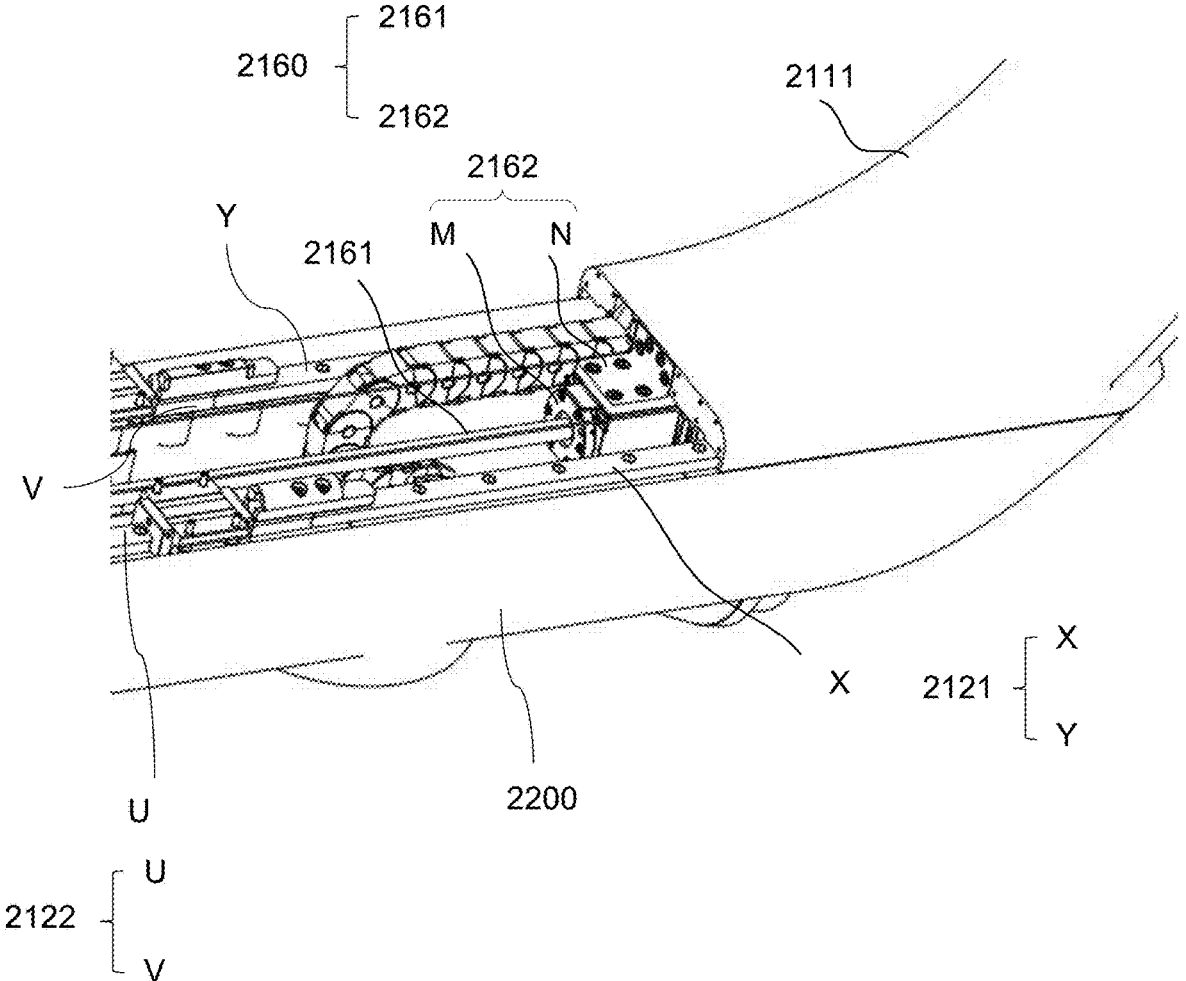
FIG. 7 is a schematic diagram illustrating an exemplary driving component according to some embodiments of the present disclosure.

In some embodiments, the first guiding section 2121 or the second guiding section 2122 may include at least two guiding units parallel to each other. For example, as illustrated in FIG. 7 (which is an enlarged view of part A in FIG. 2), the first guiding section 2121 may include at least two guiding units X and Y parallel to each other and respectively disposed on the base 2200 at intervals along a width direction of the first guiding section 2121; the second guiding section 2122 may include at least two guiding units U and V parallel to each other and respectively disposed on the base 2200 at intervals along the width direction of the second guiding section 2122. In some embodiments, the guiding unit X is collinear to the guiding unit U; the guiding unit Y is collinear to the guiding unit V. In some embodiments, the first arm section 2111 may be movably connected to the at least two guiding units X and Y, and the second arm section 2112 may be movably connected to the at least two guiding units U and V, thereby improving the assembly stability of the first arm section 2111 and the second arm section 2112 and reducing the derailment probability of the first arm section 2111 and the second arm section 2112. In some embodiments, a count of the at least two guiding units of the first guiding section 2121 may be equal to a count of the at least two guiding units of the second guiding section 2122.

In some embodiments, as shown in FIG. 3, the first arm section 2111 may be movably connected to the first guiding section 2121 via at least one first slider 2131 disposed on the first guiding section 2121; the second arm section 2112 may be movably connected to the second guiding section 2122 via at least one second slider 2132 disposed on the second guiding section 2122. In such cases, the first arm section 2111 can move toward or away from the second arm section 2112 via the at least one first slider 2131 along the first guiding section 2121; the second arm section 2112 can move toward or away from the first arm section 2111 via the at least one second slider 2132 along the second guiding section 2122; or the first arm section 2111 and the second arm section 2112 can simultaneously move toward or away from each other via the at least one first slider 2131 and the at least one second slider 2132 respectively. Accordingly, as described in connection with FIG. 1, a distance between a tube focal point inside the radiation generator and an imaging plane of the radiation detector can be adjusted by moving the first arm section 2111 and/or the second arm section 2112, thereby improving the clinical freedom degree of the C-arm-based device 2100 and meeting various clinical requirements.

In some embodiments, the at least one first slider 2131 and the at least one second slider 2132 may be detachably connected to the first arm section 2111 and the second arm section 2112 respectively. Alternatively, in order to increase connection strength, the at least one first slider 2131 and the at least one second slider 2132 may be fixedly connected to the first arm section 2111 and the second arm section 2112 respectively. Accordingly, during disassembly and maintenance, the at least one first slider 2131, the first arm section 2111, and the first guiding section 2121 can be disassembled from the base 2200 as a whole; the at least one second slider 2132, the second arm section 2112, and the second guiding section 2122 can be disassembled from the base 2200 as a whole.

In some embodiments, a first positioning shoulder (not shown) may be provided on one side of the first arm section 2111 and configured to restrict an assembly position of the at least one first slider 2131 to cause the at least one first slider 2131 to be collinear to each other; a second positioning shoulder (not shown) may be provided on one side of the second arm section 2112 and configured to restrict an assembly position of the at least one second slider 2132 to cause the at least one second slider 2132 to be collinear to each other. In addition, the first positioning shoulder and the second positioning shoulder may be collinear to each other to cause the at least one first slider 2131 to be collinear to the at least one second slider 2132, so that during disassembly and maintenance, the first arm section 2111 can be pushed onto or along the second guiding section 2122, or the second arm section 2112 can be pushed onto or along the first guiding section 2121.

Figure 4:
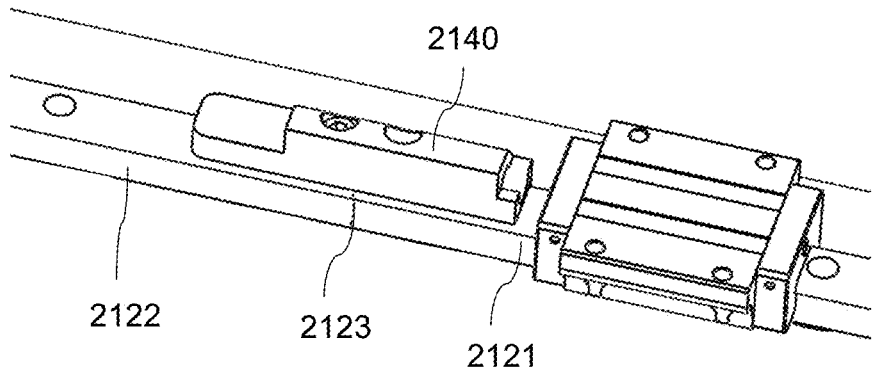
FIG. 4 is a schematic diagram illustrating an exemplary anti-collision block according to some embodiments of the present disclosure.
Figure 5:
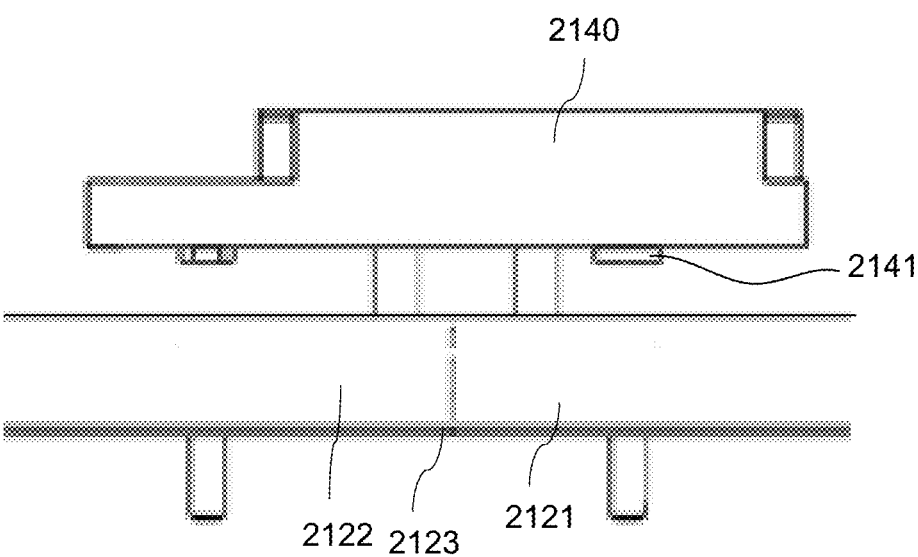
FIG. 5 is a schematic diagram illustrating an exemplary anti-collision block according to some embodiments of the present disclosure.

In some embodiments, as shown in FIG. 4 and FIG. 5, the C-arm-based device 2100 may further include an anti-collision block 2140 detachably disposed on the first guiding section 2121 and/or the second guiding section 2122. The anti-collision block 2140 may protrude toward an opening of the C-arm-based device 2100 and be configured to limit a movement range of the at least one first slider 2131 and the at least one second slider 2132 to avoid collision between the first arm section 2111 and the second arm section 2112 during the movement. In some embodiments, as shown in FIG. 4, the anti-collision block 2140 may include a first part detachably disposed on the first guiding section 2121 and a second part detachably disposed on the second guiding section 2122, accordingly, the anti-collision block 2140 may be located above the seam 2123, thereby improving the connection strength of the first guiding section 2121 and the second guiding section 2122. In some embodiments, during disassembly and maintenance, after the anti-collision block 2140 is disassembled, the first arm section 2111 may be pushed onto or along the second guiding section 2122, or the second arm section 2112 may be pushed onto or along the first guiding section 2121. In some embodiments, a material of the anti-collision block 2140 may include rubber, metal, etc.

In some embodiments, as shown in FIG. 5, the anti-collision block 2140 may include a plurality of bulges 2141 configured to position the first guiding section 2121 and/or the second guiding section 2122, thereby improving the connection strength of the base 2200 and the first guiding section 2121 and/or the second guiding section 2122.

In some embodiments, as shown in FIG. 2, the C-arm-based device 2100 may further include a stretchable protective component 2150 connected with the first arm section 2111 and the second arm section 2112 respectively. In some embodiments, the stretchable protective component 2150 may be configured to cover a space between the first arm section 2111 and the second arm section 2112 when the first arm section 2111 and the second arm section 2112 are far away from each other, thereby improving the aesthetics of the C-arm-based device 2100.

In some embodiments, two ends of the stretchable protective component 2150 may be respectively connected with the first arm section 2111 and the second arm section 2112 and extended and retracted with movements of the first arm section 2111 and the second arm section 2112. In some embodiments, when the stretchable protective component 2150 is fully retracted, a distance between the first arm section 2111 and the second arm section 2112 is the smallest; when the stretchable protective component 2150 is fully extended, the distance between the first arm section 2111 and the second arm section 2112 is the largest. In some embodiments, when components (e.g., the anti-collision block 2140, the first guiding section 2121, the second guiding section 2122, the cables in the base 2200) of the C-arm-based device 2100 covered by the stretchable protective component 2150 are maintained, the stretchable protective component 2150 need to be disassembled first.

Figure 6:
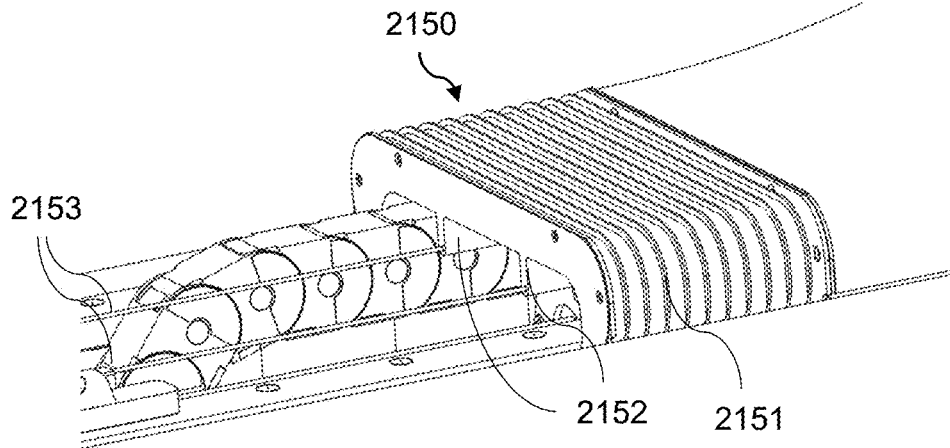
FIG. 6 is a schematic diagram illustrating an exemplary stretchable protective component according to some embodiments of the present disclosure.

In some embodiments, as shown in FIG. 6, the stretchable protective component 2150 may include a cover 2151 and a plurality of fixed units 2152 disposed under the cover 2151 at intervals (e.g., disposed under folds of the cover 2151 at intervals). In some embodiments, the fixed unit 2152 may include a fabric with a hole. In some embodiments, the stretchable protective component 2150 may be disposed through the plurality of fixed units 2152 and a fixed rope 2153 that pass through the holes of the fixed units 2152. In some embodiments, the fixed rope 2153 may be fixed on the base 2200 to prevent the stretchable protective component 2150 from being lifted by an external force. In some embodiments, the fixed rope 2153 may include a steel rope.

In some embodiments, as shown in FIG. 7, the C-arm-based device 2100 may further include at least one driving component 2160 configured to drive the first arm section 2111 and/or the second arm section 2112 to move toward or away from each other along a length direction of the connection component 2120 (e.g., the first guiding section 2121, the second guiding section 2122). In some embodiments, there may be two driving components 2160 respectively configured to drive the first arm section 2111 and the second arm section 2112 to move toward or away from each other.

In some embodiments, the driving component 2160 may include a drive acquisition mechanism and a driver configured to drive the drive acquisition mechanism to rotate to drive the first arm section 2111 and/or the second arm section 2112 to move toward or away from each other. In some embodiments, the drive acquisition mechanism may include a driving shaft 2161 connected to the driver. In some embodiments, the driver may include a motor. In some embodiments, the driver may drive the driving shaft 2161 to rotate, and the rotation of the driving shaft 2161 may be converted into a linear motion of the first arm section 2111 and/or the second arm section 2112 to drive the first arm section 2111 and/or the second arm section 2112 to move toward or away from each other. Merely by way of example, the driving shaft 2161 may drive the first arm section 2111 and/or the second arm section 2112 to move toward or away from each other by a screw-nut mechanism. In some embodiments, the movement of the first arm section 2111 and/or the second arm section 2112 may be set according to a rotation direction of the driver. For example, when the driver rotates forward, the first arm section 2111 and/or the second arm section 2112 move toward; when the driver rotates reversely, the first arm section 2111 and/or the second arm section 2112 move away from each other.

In some embodiments, as shown in FIG. 7, the driving component 2160 may further include a first fixed part 2162 and a second fixed part (not shown). The first fixed part 2162 may be configured to connect the drive acquisition mechanism (e.g., the driving shaft 2161) and the first arm section 2111. The second fixed part may be configured to connect the drive acquisition mechanism (e.g., the driving shaft 2161) and the second arm section 2112. In some embodiments, as shown in FIG. 7, the first fixed part 2162 may include two detachable portions M and N that are connected to the drive acquisition mechanism (e.g., the driving shaft 2161) and the first arm section 2111 respectively. The second fixed part may include two detachable portions that are connected to the drive acquisition mechanism (e.g., the driving shaft 2161) and the second arm section 2112 respectively.

Merely by way of example, the two detachable portions M and N of the first fixed part 2162 or the two detachable portions of the second fixed part may include a fixed block and a right-angle connecting part that are connected by screws. The fixed block may be connected to the drive acquisition mechanism (e.g., the driving shaft 2161); the right-angle connecting part may be connected to the first arm section 2111 or the second arm section 2112. During disassembly and maintenance, after the two detachable portions M and N of the first fixed part 2162 are disassembled and the anti-collision block 2140 is disassembled, the first arm section 2111 may be pushed onto the second guiding section 2122; after the two detachable portions of the second fixed part are disassembled and the anti-collision block 2140 is disassembled, the second arm section 2112 may be pushed onto the first guiding section 2121.

In some embodiments, when the first fixed part 2162 is disposed in base 2200, a height (along a direction perpendicular to the base 2200) of the fixed block of the first fixed part 2162 may be lower than a surface (towards the base 2200) of the first arm section 2111 to avoid a collision between the first arm section 2111 and the fixed block of the first fixed part 2162 when the first arm section 2111 is pushed. When the second fixed part is disposed in base 2200, a height (along a direction perpendicular to the base 2200) of the fixed block of the second fixed part may be lower than a surface (towards the base 2200) of the second arm section 2112 to avoid a collision between the second arm section 2112 and the fixed block of the second fixed part when the second arm section 2112 is pushed.

It should be noted that the above description of the C-arm-based device 2100 is merely provided for the purposes of illustration, and not intended to limit the scope of the present disclosure. For persons having ordinary skills in the art, multiple variations and modifications may be made under the teachings of the present disclosure.

During the development of the medical robot (e.g., a digital subtraction angiography (DSA) robot), a count of the movable arm sections has been upgraded from one to two, which improves the flexibility of clinical applications. The upgrade of the movable arm sections means that a driving component used to drive the movement of the arm sections is more complicated, resulting in large structural dimensions, heavy weight, and poor serviceability. Generally, two movable arm sections are driven to move by two driving components respectively, which is simple in control and structure, but leads to large volume, high weight, poor serviceability, and additional material cost.

Figure 8:
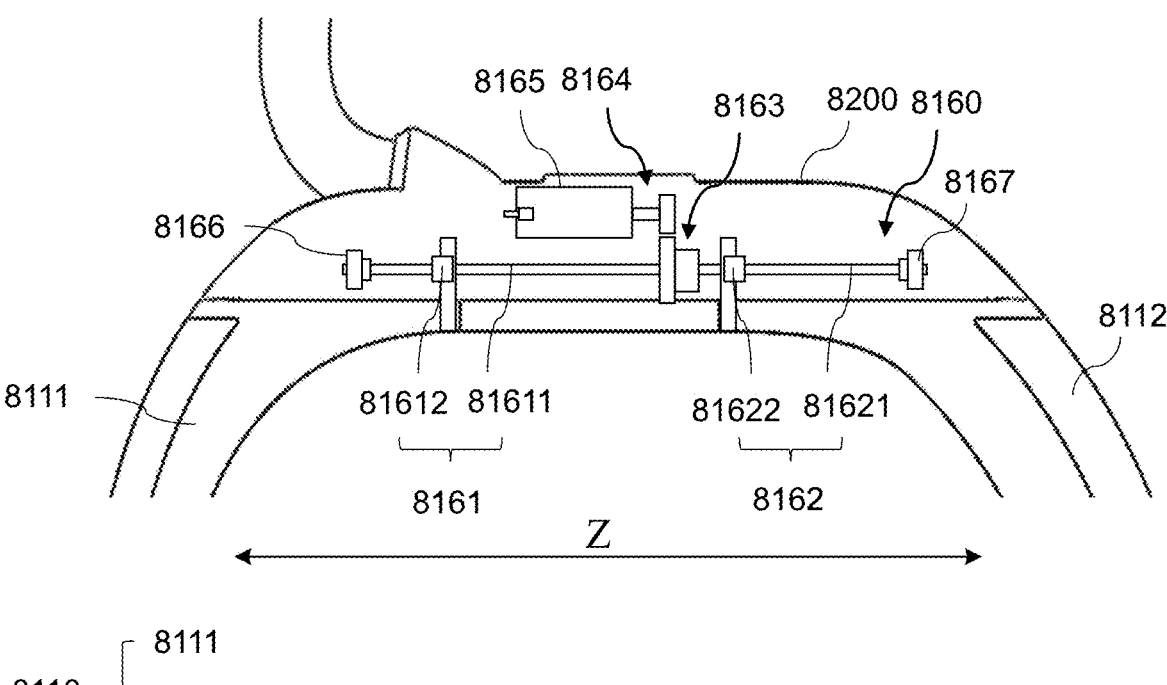
FIG. 8 is a schematic diagram illustrating an exemplary C-arm-based device and an exemplary driving component thereof according to some embodiments of the present disclosure.

FIG. 8 is a schematic diagram illustrating an exemplary C-arm-based device and an exemplary driving component thereof according to some embodiments of the present disclosure. In some embodiments, the C-arm-based device 8100 may be an exemplary embodiment of the C-arm-based device 2100 illustrated in FIG. 2 or the C-arm-based device 1100 illustrated in FIG. 1. In some embodiments, the C-arm-based device 8100 may be an exemplary independent embodiment of the C-arm-based device described in the present disclosure.

As shown in FIG. 8, the C-arm-based device 8100 may include a C-arm component 8110 and a connection component (not shown). The C-arm component 8110 may include a first arm section 8111 and a second arm section 8112. The first arm section 8111 and the second arm section 8112 may be assembled with each other to form the C-arm component 8110. The connection component may be disposed on a base 8200 (which may be an exemplary embodiment of the based 1200 illustrated in FIG. 1 or the base 2200 illustrated in FIG. 2 or an exemplary independent embodiment of the base described in the present disclosure) and located between the first arm section 8111 and the second arm section 8112. More detailed descriptions of the C-arm component 8110 or the connection component may be found elsewhere in the present disclosure, for example, FIGS. 2-7 and descriptions thereof.

In some embodiments, as shown in FIG. 8, the C-arm-based device 8100 may further include a driving component 8160. In some embodiments, the driving component 8160 may be an exemplary embodiment of the driving component 2160 of the C-arm-based device 2100 illustrated in FIG. 7. In some embodiments, the driving component 8160 may be an exemplary independent embodiment of the driving component described in the present disclosure. In some embodiments, the driving component 8160 may disposed in the base 8200.

In some embodiments, the driving component 8160 may include a first drive conversion mechanism 8161 connected to the first arm section 8111, a second drive conversion mechanism 8162 connected to the second arm section 8112, a drive transmission mechanism 8163 connected with the first drive conversion mechanism 8161 and the second drive conversion mechanism 8162, a drive acquisition mechanism 8164 (which may be an exemplary embodiment of the drive acquisition mechanism described above or an exemplary independent embodiment of the drive acquisition mechanism described in the present disclosure), and a driver 8165 (e.g., which may be an exemplary embodiment of the driver described above or an exemplary independent embodiment of the driver described in the present disclosure).

In some embodiments, the drive transmission mechanism 8163 may be configured to transmit drive of the drive acquisition mechanism 8164 to the first drive conversion mechanism 8161 and/or the second drive conversion mechanism 8162 to guide the first drive conversion mechanism 8161 and/or the second drive conversion mechanism 8162 to move to drive the first arm section 8111 and/or the second arm section 8112 to move toward or away from each other along a direction Z, thereby increasing or decreasing a distance between the first arm section 8111 and the second arm section 8112 to meet various clinical requirements.

In some embodiments, the first drive conversion mechanism 8161 may include a main conversion assembly 81611 and a secondary conversion assembly 81612; the second drive conversion mechanism 8162 may include a main conversion assembly 81621 and a secondary conversion assembly 81622. The main conversion assembly 81611 and the main conversion assembly 81621 may be connected with the drive transmission mechanism 8163, and the drive transmission mechanism 8163 may drive the main conversion assembly 81611 and the main conversion assembly 81621 to rotate. The secondary conversion assembly 81612 may be connected with the main conversion assembly 81611 and the first arm section 8111, and the main conversion assembly 81611 may convert rotation of the main conversion assembly 81611 into a linear motion of the secondary conversion assembly 81612 to drive the first arm section

8111. The secondary conversion assembly 81622 may be connected with the main conversion assembly 81621 and the second arm section 8112, and the main conversion assembly 81621 may convert rotation of the main conversion assembly 81621 into a linear motion of the secondary conversion assembly 81622 to drive the second arm section 8112.

In some embodiments, the first drive conversion mechanism 8161 or the second drive conversion mechanism 8162 may include a screw-nut mechanism. The main conversion assembly 81611 or the main conversion assembly 81621 may be a screw; and the secondary conversion assembly 81612 or the secondary conversion assembly 81622 may be a nut. The screw may extend along the direction Z, and the nut may be sleeved on the screw by means of threaded connection. The rotation of the screw may be converted into a linear motion of the nut, thereby driving the first arm section 8111 or the second arm section 8112 to move along the direction Z.

In some embodiments, the first drive conversion mechanism 8161 or the second drive conversion mechanism 8162 may include a gear-rack mechanism. The main conversion assembly 81611 or the main conversion assembly 81621 may be a gear; and the secondary conversion assembly 81612 or the secondary conversion assembly 81622 may be a rack. The rack may extend along the direction Z, and the rack may be driven by the rotation of the gear to move, thereby driving the first arm section 8111 or the second arm section 8112 to move along the direction Z.

It should be noted that the above screw-nut mechanism and the gear-rack mechanism are merely provided for the purposes of illustration, and not intended to limit the scope of the present disclosure. Any mechanism that can convert rotation into linear motion may be used as the first drive conversion mechanism 8161 or the second drive conversion mechanism 8162. In some embodiments, the first drive conversion mechanism 8161 and the second drive conversion mechanism 8162 may be the same or different mechanisms. For example, both the first drive conversion mechanism 8161 and the second drive conversion mechanism 8162 are the screw-nut mechanism. As another example, the first drive conversion mechanism 8161 is the screw-nut mechanism, and the second drive conversion mechanism 8162 is the gear-rack mechanism.

In some embodiments, in response to that the drive transmission mechanism 8163 simultaneously guides the first drive conversion mechanism 8161 and the second drive conversion mechanism 8162 to move, the secondary conversion assembly 81612 of the first drive conversion mechanism 8161 and the secondary conversion assembly 81622 of the second drive conversion mechanism 8162 may move in opposite directions to drive the first arm section 8111 and the second arm section 8112 to move in the opposite directions, thereby increasing or decreasing a distance between the first arm section 8111 and the second arm section 8112. In some embodiments, a technician may assemble the first drive conversion mechanism 8161 and the second drive conversion mechanism 8162 to realize that the main conversion assembly 81611 and the main conversion assembly 81621 drive the secondary conversion assembly 81612 and the secondary conversion assembly 81622 to move in the opposite directions. For example, when both the first drive conversion mechanism 8161 and the second drive conversion mechanism 8162 are the screw-nut mechanism, helical directions of the two screws may be set as the same to realize that the two screws drive the two nuts to move in the opposite directions.

In some embodiments, moving speeds of the first arm section 8111 and the second arm section 8112 may be different or the same, accordingly, moving speeds of the secondary conversion assembly 81612 and the secondary conversion assembly 81622 may be different or the same. In some embodiments, a moving speed of the secondary conversion assembly 81612 may be adjusted by adjusting a lead of the main conversion assembly 81611; and a moving speed of the secondary conversion assembly 81622 may be adjusted by adjusting a lead of the main conversion assembly 81621. A lead may refer to a distance that the main conversion assembly 81611 or the main conversion assembly 81621 rotates once to drive the secondary conversion assembly 81612 or the secondary conversion assembly 81622 to move. For example, when the first drive conversion mechanism 8161 or the second drive conversion mechanism 8162 includes the screw-nut mechanism, a lead of the screw may refer to a distance that the screw rotates once to drive the nut to move.

In some embodiments, in response to that the drive transmission mechanism 8163 simultaneously guides the first drive conversion mechanism 8161 and the second drive conversion mechanism 8162 to move, the secondary conversion assembly 81612 of the first drive conversion mechanism 8161 and the secondary conversion assembly 81622 of the second drive conversion mechanism 8162 may move in a same direction to drive the first arm section 8111 and the second arm section 8112 to move in the same directions. Moving speeds of the secondary conversion assembly 81612 and the secondary conversion assembly 81622 may be different or the same, thereby increasing or decreasing a distance between the first arm section 8111 and the second arm section 8112. In some embodiments, the technician may assemble the first drive conversion mechanism 8161 and the second drive conversion mechanism 8162 to realize that the main conversion assembly 81611 and the main conversion assembly 81621 drive the secondary conversion assembly 81612 and the secondary conversion assembly 81622 to move in the same direction. For example, when both the first drive conversion mechanism 8161 and the second drive conversion mechanism 8162 are the gear-rack mechanism, rotation directions of the two gears may be set as the same to realize that the two gears drive the two racks to move in the same direction.

In some embodiments, different moving speeds of the secondary conversion assembly 81612 and the secondary conversion assembly 81622 may be obtained by configuring the leads of the main conversion assembly 81611 and the main conversion assembly 81621. For example, when the lead of the main conversion assembly 81611 is larger than the lead of the main conversion assembly 81621, the moving speed of the secondary conversion assembly 81612 may be larger than the moving speed of the secondary conversion assembly 81622. In such case, when the secondary conversion assembly 81612 and the secondary conversion assembly 81622 are both moved toward the first arm section 8111, the distance between the first arm section 8111 and the second arm section 8112 may be increased; when the secondary conversion assembly 81612 and the secondary conversion assembly 81622 are both moved toward the second arm section 8112, the distance between the first arm section 8111 and the second arm section 8112 may be decreased. In some embodiments, when configuring the first drive conversion mechanism 8161 and the second drive conversion mechanism 8162, the technician may configure the leads of the main conversion assembly 81611 and the main conversion assembly 81621 based on the requirements of the moving speeds of the first arm section 8111 and the second arm section 8112.

In some embodiments, the driving component 8160 may further include two brakes 8166 and 8167 respectively configured to stop or release the rotation of the main conversion assemblies 81611 and 81621 of the first drive conversion mechanism 8161 and the second drive conversion mechanism 8162. In some embodiments, the brake 8166 and/or brake 8169 may include an electromagnet. When being energized, the brake 8166 and/or brake 8167 may generate magnetic forces to stop the rotation of the main conversion assemblies 81611 and 81621. When the brakes 8166 and 8167 respectively release the rotation of the main conversion assemblies 81611 and 81621 of the first drive conversion mechanism 8161 and the second drive conversion mechanism 8162, the first drive conversion mechanism 8161 and the second drive conversion mechanism 8162 may respectively drive the first arm section 8111 and the second arm section 8112 to move toward or away from each other. When the brake 8166 stops the rotation of the main conversion assembly 81611 of the first drive conversion mechanism 8161 and the brake 8167 releases the rotation of the main conversion assembly 81621 of the second drive conversion mechanism 8162, the second drive conversion mechanism 8162 may drive the second arm section 8112 to move toward or away from the first arm section 8111. When the brake 8166 releases the rotation of the main conversion assembly 81611 of the first drive conversion mechanism 8161 and the brake 8167 stops the rotation of the main conversion assembly 81621 of the second drive conversion mechanism 8162, the first drive conversion mechanism 8161 may drive the first arm section 8111 to move toward or away from the second arm section 8112.

According to the embodiments of the present disclosure, there is no need to configure two independent driving components, one driving component 8160 can drive the first arm section 8111 and the second arm section 8112 to move toward or away from each other, which saves material cost, reduces size and weight of the C-arm-based device 8100, and improves serviceability of the C-arm-based device 8100. In addition, the movement of the first arm section 8111 and the second arm section 8112 does not require the coordination of a robot body (e.g., the robot body 1300 illustrated in FIG. 1), which simplifies the decoupling of the control of the first arm section 8111 and the second arm section 8112 and improves clinical freedom.

Figure 9:
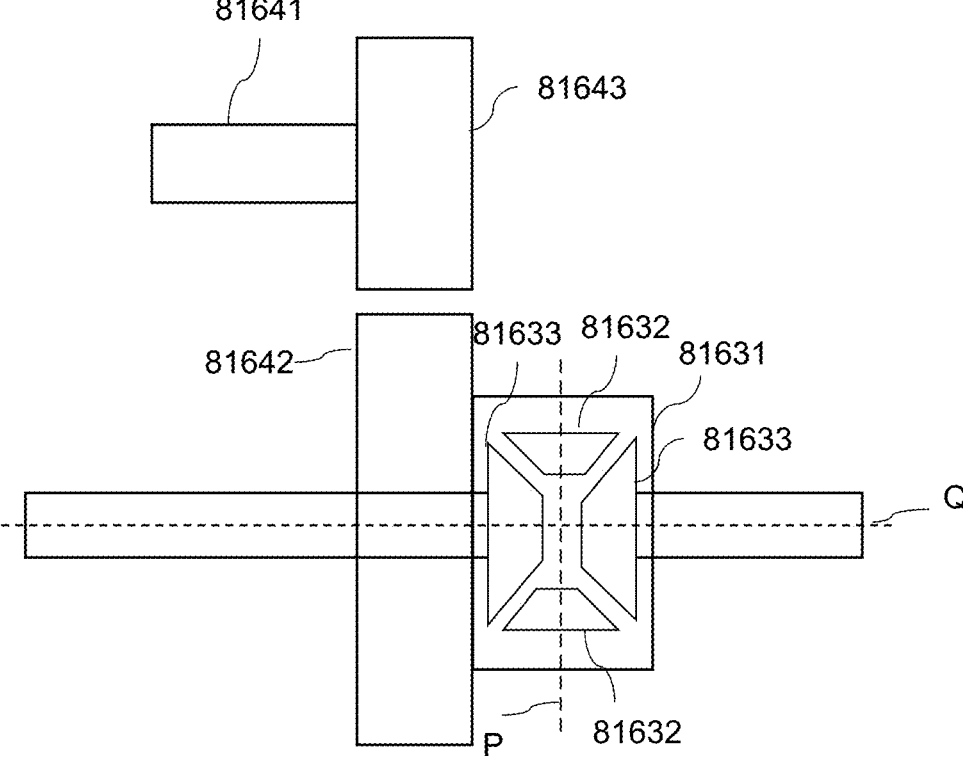
FIG. 9 is a schematic diagram illustrating exemplary structures of an exemplary drive transmission mechanism and an exemplary drive acquisition mechanism according to some embodiments of the present disclosure.

FIG. 9 is a schematic diagram illustrating exemplary structures of an exemplary drive transmission mechanism and an exemplary drive acquisition mechanism according to some embodiments of the present disclosure.

As shown in FIG. 9, the drive transmission mechanism 8163 may include a first rotating wheel 81631, at least one first bevel gear 81632 disposed in the first rotating wheel 81631, and two second bevel gears 81633 meshing with the at least one first bevel gear 81632.

In some embodiments, a central axis P of the at least one first bevel gear 81632 may be perpendicular to a central axis Q of the first rotating wheel 81631. The first rotating wheel 81631 may rotate (around the central axis Q) to drive the at least one first bevel gear 81632 to rotate around the central axis Q of the first rotating wheel 81631. The at least one first bevel gear 81632 may mesh with the two second bevel gears 81633 to drive the two second bevel gears 81633 to rotate around the central axis Q of the first rotating wheel 81631. In some embodiments, the drive transmission mechanism

8163 may include at least two first bevel gears 81632 to increase the drive for the two second bevel gears 81633. In some embodiments, as shown in FIG. 9, the at least two first bevel gears 81632 may be symmetrically arranged, and their central axes coincide.

In some embodiments, the two second bevel gears 81633 may be coaxial with the first rotating wheel 81631 and respectively coaxially fixed with main conversion assemblies 81611 and 81621 of the first drive conversion mechanism 8161 and the second drive conversion mechanism 8162 to respectively guide the first drive conversion mechanism 8161 and the second drive conversion mechanism 8162 to move. In some embodiments, the drive transmission mechanism 8163 may include a clutch. It should be noted that when the main conversion assemblies 81611 and/or 81621 are stopped by brakes (e.g., brakes 8166 and/or 8167), the at least one first bevel gear 81632 still rotates around its central axis P.

In some embodiments, the drive acquisition mechanism 8164 may drive the first rotating wheel 81631 to rotate around the central axis Q to drive the at least one first bevel gear 81632 to rotate around the central axis Q of the first rotating wheel 81631. The at least one first bevel gear 81632 may drive the two second bevel gears 81633 to rotate around the central axis Q of the first rotating wheel 81631 to respectively guide the main conversion assemblies 81611 and 81621 of the first drive conversion mechanism 8161 and the second drive conversion mechanism 8162 to rotate. The rotations of the main conversion assemblies 81611 and 81621 may be respectively converted into linear motions of the secondary conversion assemblies 81612 and 81622 to drive the first arm section 8111 or the second arm section 8112. In some embodiments, when the main conversion assembly 81621 of the second drive conversion mechanism 8162 is stopped, the second bevel gear 81633 coaxially fixed with the main conversion assembly 81621 is also stopped. Accordingly, the at least one first bevel gear 81632 can't drive the second bevel gear 81633 coaxially fixed with the main conversion assembly 81621 to rotate. In such cases, the at least one first bevel gear 81632 may rotate around its central axis P and the central axis Q of the first rotating wheel 81631, so that the at least one first bevel gear 81632 may roll around a circumference of the second bevel gear 81633 coaxially fixed with the main conversion assembly 81621 while driving the second bevel gear 81633 fixed with the main conversion assembly 81611 to rotate, thereby avoiding being stuck by the second bevel gear 81633 coaxially fixed with the main conversion assembly 81611.

As shown in FIG. 9, the drive acquisition mechanism 8164 may include a driving shaft 81641, a second rotating wheel 81642, and a third rotating wheel 81643. In some embodiments, the driving shaft 81641 may be an exemplary embodiment of the driving shaft 2161 illustrated in FIG. 7 or may be an exemplary independent embodiment described in the present disclosure. In some embodiments, the driving shaft 81641 may be connected to the driver 8165 or an external driver disposed outside the C-arm-based device 8100 and transmit the drive of the driver 8165 or the external driver to the third rotating wheel 81643 to drive the third rotating wheel 81643 to rotate. The third rotating wheel 81643 may be fixed coaxially with the driving shaft 81641 and mesh with the second rotating wheel 81642 to drive the second rotating wheel 81642 to rotate. The second rotating wheel 81642 may be fixed coaxially with the first rotating wheel 81631 to drive the first rotating wheel 81631 to rotate.

It should be noted that the above description of the C-arm-based device 8100 is merely provided for the purposes of illustration, and not intended to limit the scope of the present disclosure. For persons having ordinary skills in the art, multiple variations and modifications may be made under the teachings of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.), or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A computer-readable signal medium may include a propagated data signal with computer-readable program code embodied therein, for example, in a baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction-performing system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python, or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer, and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A C-arm-based device, comprising:
a C-arm component including a first arm section and a second arm section;
a connection component including a first guiding section and a second guiding section separately disposed on a base, wherein
the first arm section is movably connected to the first guiding section;
the second arm section is movably connected to the second guiding section;
the first guiding section and the second guiding section are separately and detachably disposed on the base,
the first guiding section and the second guiding section are collinear to each other, and
the first guiding section and the second guiding section abut against each other.

2. The C-arm-based device of claim 1, wherein the first guiding section or the second guiding section includes two guiding units parallel to each other.

3. The C-arm-based device of claim 1, wherein
the first arm section is movably connected to the first guiding section via at least one first slider disposed on the first guiding section; and
the second arm section is movably connected to the second guiding section via at least one second slider disposed on the second guiding section.

4. The C-arm-based device of claim 1, wherein the C-arm-based device further includes a stretchable protective component connected with the first arm section and the second arm section respectively.

5. The C-arm-based device of claim 1, wherein the C-arm-based device further includes a driving component configured to drive the first arm section and/or the second arm section to move toward or away from each other along a length direction of the connection component, and the driving component includes a drive acquisition mechanism and a driver configured to drive the drive acquisition mechanism to rotate to drive the first arm section and/or the second arm section to move toward or away from each other.

6. The C-arm-based device of claim 5, wherein the driving component further includes a first fixed part and a second fixed part, the first fixed part including two detachable portions that are connected to the drive acquisition mechanism and the first arm section respectively, the second fixed part including two detachable portions that are connected to the drive acquisition mechanism and the second arm section respectively.

7. The C-arm-based device of claim 5, wherein the driving component further includes:

a first drive conversion mechanism connected to the first arm section;
a second drive conversion mechanism connected to the second arm section; and
a drive transmission mechanism connected with the first drive conversion mechanism and the second drive conversion mechanism, wherein the drive transmission mechanism is configured to transmit drive of the drive acquisition mechanism to the first drive conversion mechanism and/or the second drive conversion mechanism to guide the first drive conversion mechanism and/or the second drive conversion mechanism to move to drive the first arm section and/or the second arm section to move toward or away from each other.

8. The C-arm-based device of claim 7, wherein at least one of the first drive conversion mechanism and the second drive conversion mechanism includes:
a main conversion assembly connected with the drive transmission mechanism, wherein the drive transmission mechanism drives the main conversion assembly to rotate; and
a secondary conversion assembly connected with the main conversion assembly and the first arm section or the second arm section, wherein the main conversion assembly converts rotation of the main conversion assembly into a linear motion of the secondary conversion assembly to drive the first arm section or the second arm section.

9. The C-arm-based device of claim 8, wherein in response to that the drive transmission mechanism simultaneously guides the first drive conversion mechanism and the second drive conversion mechanism to move, the secondary conversion assemblies of the first drive conversion mechanism and the second drive conversion mechanism move in opposite directions.

10. The C-arm-based device of claim 8, wherein in response to that the drive transmission mechanism simultaneously guides the first drive conversion mechanism and the second drive conversion mechanism to move, the secondary conversion assemblies of the first drive conversion mechanism and the second drive conversion mechanism move in a same direction, moving speeds of the secondary conversion assemblies being different or the same.

11. The C-arm-based device of claim 8, wherein
the first drive conversion mechanism or the second drive conversion mechanism includes a screw-nut mechanism, wherein the main conversion assembly is a screw and the secondary conversion assembly is a nut; or
the first drive conversion mechanism or the second drive conversion mechanism includes a gear-rack mechanism, wherein the main conversion assembly is a gear and the secondary conversion assembly is a rack.

12. The C-arm-based device of claim 8, wherein the drive transmission mechanism includes a first rotating wheel, at least one first bevel gear disposed in the first rotating wheel, and two second bevel gears meshing with the at least one first bevel gear, wherein
a central axis of the at least one first bevel gear is perpendicular to a central axis of the first rotating wheel, wherein the first rotating wheel rotates to drive the at least one first bevel gear to rotate around the central axis of the first rotating wheel; and
the two second bevel gears are coaxial with the first rotating wheel and respectively coaxially fixed with main conversion assemblies of the first drive conversion mechanism and the second drive conversion mechanism to respectively guide the first drive conversion mechanism and the second drive conversion mechanism to move.

13. The C-arm-based device of claim 12, wherein the drive acquisition mechanism includes:

a driving shaft;

a second rotating wheel fixed coaxially with the first rotating wheel; and a third rotating wheel meshing with the second rotating wheel and fixed coaxially with the driving shaft.

14. The C-arm-based device of claim 8, wherein the driving component further includes two brakes respectively configured to stop or release the rotation of the main conversion assemblies of the first drive conversion mechanism and the second drive conversion mechanism.

15. The C-arm-based device of claim 1, wherein further comprising a single driving component configured to drive the first arm section and the second arm section to move toward or away from each other along a length direction of the connection component.

16. The C-arm-based device of claim 1, wherein there is a seam between the first guiding section and the second guiding section, a distance between the seam and a center line of the base is larger than a distance threshold.

17. The C-arm-based device of claim 16, wherein the C-arm-based device further includes an anti-collision block detachably disposed on the first guiding section and the second guiding section, and the anti-collision block is located above the seam.

18. The C-arm-based device of claim 1, wherein the first guiding section includes a first guiding unit and a second guiding unit parallel to each other, the second guiding section includes a third guiding unit and a fourth guiding unit parallel to each other, the first guiding unit is collinear to the third guiding unit, and the second guiding unit is collinear to the fourth guiding unit.

19. A medical device, comprising:

a base;

a C-arm-based device including:

a C-arm component including a first arm section and a second arm section;

a connection component including a first guiding section and a second guiding section separately disposed on the base, wherein the first arm section is movably connected to the first guiding section;

the second arm section is movably connected to the second guiding section;

the first guiding section and the second guiding section are separately and detachably disposed on the base, the first guiding section and the second guiding section are collinear to each other, and the first guiding section and the second guiding section abut against each other; and a robot body rotatably connected to the base and configured to drive the C-arm-based device to move in space.

20. A C-arm-based device, comprising a C-arm component including:

a first arm section and a second arm section;

a connection component connected between the first arm section and the second arm section; and a single driving component configured to drive the first arm section and the second arm section to move toward or away from each other along a length direction of the connection component and including:

a drive acquisition mechanism configured to acquire drive;

a first drive conversion mechanism connected to the first arm section;

a second drive conversion mechanism connected to the second arm section; and a drive transmission mechanism connected with the first drive conversion mechanism and the second drive conversion mechanism, wherein the drive transmission mechanism is configured to transmit the drive of the drive acquisition mechanism to the first drive conversion mechanism and the second drive conversion mechanism to guide the first drive conversion mechanism and the second drive conversion mechanism to move to drive the first arm section and the second arm section to move toward or away from each other.

* * * * *